US011284815B2

United States Patent
Carlsgaard et al.

(10) Patent No.: US 11,284,815 B2
(45) Date of Patent: Mar. 29, 2022

(54) BOLUS CALCULATOR TIME KEEPING BETWEEN MOBILE PHONE APPLICATION AND BG METERS

(71) Applicant: Roche Diagnostics Operations, Inc., Indianapolis, IN (US)

(72) Inventors: Eric S. Carlsgaard, Zionsville, IN (US); Paul J. Galley, Cumberland, IN (US); Mark G. Mears, Westfield, IN (US); Benoit P. Menez, Carmel, IN (US); Hemlata Nayee, Fishers, IN (US); Jose Salazar-Galindo, Noblesville, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 1330 days.

(21) Appl. No.: 14/242,953

(22) Filed: Apr. 2, 2014

(65) Prior Publication Data
US 2014/0321246 A1 Oct. 30, 2014

Related U.S. Application Data

(60) Provisional application No. 61/816,462, filed on Apr. 26, 2013, provisional application No. 61/816,542, filed on Apr. 26, 2013.

(51) Int. Cl.
*A61B 5/145* (2006.01)
*G06F 16/27* (2019.01)
*G16H 40/63* (2018.01)
*G16H 40/67* (2018.01)

(52) U.S. Cl.
CPC .......... *A61B 5/14532* (2013.01); *G06F 16/27* (2019.01); *G16H 40/63* (2018.01); *G16H 40/67* (2018.01)

(58) Field of Classification Search
CPC .... G06Q 50/22; G06Q 50/24; A61B 5/14532; G06F 16/27; G16H 40/63; G16H 40/67
USPC ........................................ 705/2–3
See application file for complete search history.

(56) References Cited

U.S. PATENT DOCUMENTS

| 5,216,597 | A | 6/1993 | Beckers |
| 8,583,956 | B2 | 11/2013 | Fong et al. |
| 2005/0038674 | A1 | 2/2005 | Braig et al. |
| 2006/0010098 | A1 | 1/2006 | Goodnow et al. |
| 2009/0158274 | A1 | 6/2009 | Roberts |
| 2010/0010581 | A1* | 1/2010 | Goetz ............... A61M 5/14276 607/60 |

(Continued)

FOREIGN PATENT DOCUMENTS

| CN | 102201029 A | 9/2011 |
| CN | 102355852 A | 2/2012 |

*Primary Examiner* — Eliza A Lam

(57) ABSTRACT

A diabetes management system includes a handheld medical device, a mobile computing device, and a diabetes management application. The handheld medical device is configured to measure glucose in a sample of fluid residing in a test strip and associate a measurement time with the glucose measurement. The diabetes management application is configured to request a current device time from the RTC, determine a first device delta time by determining a difference between the current device time and an internal clock time, and associate a first timestamp with a glucose measurement, wherein the first timestamp is equal to the measurement time plus the first device delta time.

17 Claims, 11 Drawing Sheets

(56) References Cited

U.S. PATENT DOCUMENTS

| | | |
|---|---|---|
| 2010/0299457 A1 | 11/2010 | Johnson |
| 2011/0124996 A1 | 5/2011 | Reinke et al. |
| 2012/0310669 A1 | 12/2012 | Carlberg et al. |
| 2013/0230041 A1 | 9/2013 | Han et al. |
| 2014/0066884 A1* | 3/2014 | Keenan ................ A61M 5/172 604/504 |
| 2014/0142540 A1* | 5/2014 | Imhof ................ G06F 19/3412 604/504 |

* cited by examiner

BOLUS CALCULATOR TIME KEEPING BETWEEN MOBILE PHONE APPLICATION AND BG METERS

CROSS-REFERENCE TO RELATED APPLICATIONS

This application claims the benefit of U.S. Provisional Application No. 61/816,462, filed on Apr. 26, 2013 and U.S. Provisional Application No. 61/816,542, filed on Apr. 26, 2013. The entire disclosures of each of the above applications are incorporated herein by reference.

FIELD

The present disclosure relates to techniques for transferring data from a handheld glucose meter automatically and seamlessly to a portable communication device.

BACKGROUND

Persons with diabetes have difficulty regulating blood glucose levels in their bodies. As a consequence, many of these persons carry specialized electronic meters, called blood glucose meters, which allow them to periodically measure their glucose levels and take appropriate action, such as administering insulin or ingesting carbohydrates. These persons may also carry with them a portable communication device, such as a mobile phone, a personal digital assistant, a tablet or similar device. People often rely on their portable communication device as the primary means for planning, scheduling and communicating with others. As a result, most portable communication devices are equipped with sophisticated software which provides user-friendly means for viewing and inputting data. Accordingly, a person with diabetes may wish to wirelessly transmit the results of a blood glucose measurement from their glucose meter to their portable communications device in order, for example, to display, analyze or report on the data.

The blood glucose measurements each include a timestamp indicating when the measurement was taken. The portable device utilizes the timestamps in order to analyze the measurements. Each of the glucose meter and the portable communication device include a means for tracking time, such as an internal digital clock. The glucose meter and the portable device may also include a user adjustable clock. Because of inherent inaccuracies between the multiple clocks, it is desirable to develop improved techniques for time keeping between the glucose meter and the portable communication device.

This section provides background information related to the present disclosure which is not necessarily prior art.

SUMMARY

Persons with diabetes often carry a handheld glucose meter as well as a portable computing device, such as a mobile phone. Given the close proximity of these two devices, the portable computing device can serve as a data collector for the glucose measures taken by the glucose meter. Improved techniques are set forth for time keeping between a glucose meter and a patient's portable communication device.

A diabetes management system includes a handheld medical device, a mobile computing device, and a diabetes management application. The handheld medical device includes a port configured to receive a test strip having a reaction site for receiving a sample of fluid from a patient, a real-time clock (RTC), and a blood glucose (bG) meter, cooperatively operable with a test strip inserted in the port, configured to measure glucose in a sample of fluid residing in the test strip and associate a first measurement time with the glucose measurement.

The computing device includes a processor configured to execute a diabetes management application stored on an associated memory and a counter that begins counting time in response to the mobile computing device being initiated. The diabetes management application is configured to determine a snapshot time, set an internal clock of the diabetes management application equal to the snapshot time and keep time on the internal clock by using the counter, determine whether the handheld medical device is paired with the mobile computing device, and selectively instruct the handheld medical device to communicate the glucose measurement and the first measurement time in response to a determination that the handheld medical device is paired with the mobile computing device.

The diabetes management application is further configured to request a current device time from the RTC on the handheld medical device, determine a first device delta time by determining a difference between the current device time and a time on the internal clock, and associate a first timestamp with the glucose measurement, wherein the first timestamp is equal to the first measurement time plus the first device delta time.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

DRAWINGS

FIG. 9 depicts exemplary screenshots of the diabetes management application;

FIG. 10 depicts further exemplary screenshots of the diabetes management application; and FIG. 11 depicts further exemplary screenshots of the diabetes management application.

Figure 1:
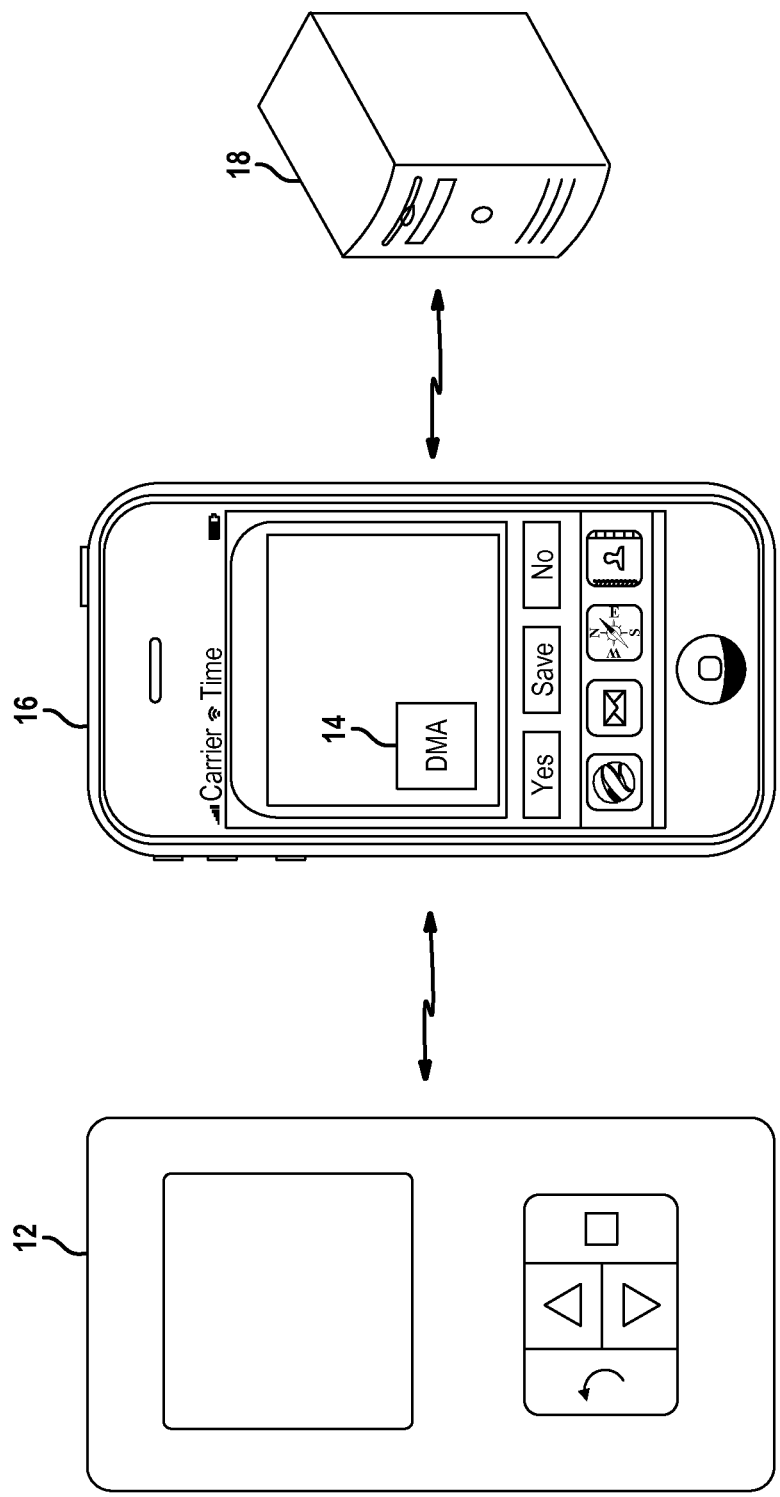
FIG. 1 is a diagram depicting a handheld glucose meter in data communication with a diabetes management application residing on a mobile phone.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

FIG. 1 depicts an exemplary handheld glucose meter 12 in data communication via a wireless data link with a diabetes management application 14. The glucose meter 12 is configured to receive a sample of blood from a patient and determine a blood glucose measure for the patient from the blood sample. One or more blood glucose measures may in turn be transmitted over the wireless data link to the diabetes management application 14 for further processing. In an exemplary embodiment, the diabetes management application 14 resides on a mobile phone 16. In other embodiments, the diabetes management application 14 may be native to a remote server 18 with its user interface presented on the mobile phone 16.

The mobile phone 16 may be a handheld computing device arranged to include a hardware layer, an operating system layer, an application layer, and a user interface layer. For example, the hardware layer includes a processor and memory. The operating system layer includes an operating system. The operating system is a set of instructions stored in memory and executed by the processor. For example only, the operating system may include Android OS, iOS, or any other suitable mobile phone or tablet operating system. The application layer includes at least one software application, for example the diabetes management application 14. The user interface layer includes a user input device, such as a keyboard or a touch screen interface, and a display screen.

In some embodiments, data is transferred to and from the glucose meter 12 using the Bluetooth wireless technology standard (e.g., low energy feature of Bluetooth 4.0) although other types of communication transports are contemplated by this disclosure. For example only, data may be transferred to and from the glucose meter 12 using a WiFi network connection or a physical cable connection. In some embodiments, the glucose meter 12 is physically connected to a personal computer (PC). The glucose meter 12 transfers data over the physical connection and is stored in memory within the PC. The PC may be configured to transmit data received from the glucose meter 12 to another computing device, such as the mobile phone 16. In another embodiment, the PC may be configured to transmit data received from the glucose meter 12 to the remote server 18. The mobile phone 16 may then communicate with the remote server 18. For example, the remote server 18 may transmit data to the mobile phone 16. The mobile phone 16 stores the received data. The diabetes management application 14 may process the data stored within the mobile phone 16.

In other embodiments, the mobile phone 16 may communicate the one or more glucose measures to the remote server 18. For example, the mobile phone 16 may be configured to determine whether to communicate the one or more glucose measures to the remote server 18. Upon receiving the one or more glucose measures from the meter 12, the mobile phone 16 determines whether to communicate the one or more glucose measures to the remote server 18. In some embodiments, the mobile phone 16 is configured to automatically communicate the one or more glucose measures to the remote server 18.

In yet another embodiment, the mobile phone 16 is configured to determine whether the remote server 18 has sent a glucose measure request to the mobile phone 16. When the mobile phone 16 determines the remote server 18 has sent a glucose measure request to the mobile phone 16, the mobile phone 16 communicates the one or more glucose measures to the remote server 18. The glucose measure request may be a signal communicated over a wireless network to the mobile phone 16.

The remote server 18 stores the one or more glucose measures in memory within the remote server 18. The remote server 18 may perform further processing on the one or more glucose measures. For example, the remote server 18 associates the one or more glucose measures with other data relevant to the patient such as patient name, patient age, the date and time the one or more glucose measures were collected, patient measurement history, and any other relevant data. The remote server 18 is configured to allow remote access to data stored within the remote server 18. For example, a physician of the patient may access the one or more glucose measures stored on in order to treat the patient. It is understood that while only the one or more glucose measures is discussed, the principles described herein also apply to any patient data received by the glucose meter 12, the diabetes management application 14, and the mobile phone 16.

In some embodiments, the diabetes management application 14 includes an insulin bolus calculator. For example, the diabetes management application 14 may receive the one or more glucose measures and a measurement time associated with each other the one or more glucose measures from the glucose meter 12. The diabetes management application 14 determines a bolus calculation based on the one or more glucose measures. Further discussions of the bolus calculator can be found in the commonly assigned U.S. patent application Ser. No. 13/593,593, filed Aug. 24, 2012, the entire disclosure of which is hereby incorporated by reference.

In another embodiment, the diabetes management application 14 is configured to keep time between the meter 12 and the mobile phone 16. For example, the meter 12 includes a real-time clock (RTC). The RTC is internal to the meter 12. The RTC is set when the meter 12 is initiated. For example, the RTC is set when the meter 12 is initially setup by the patient. The RTC is unaffected by changes made to the meter 12 by the patient. For example, the patient may change a display clock of the meter 12. The display clock may represent the current local time of the meter 12. The patient may adjust the display clock when traveling between time zones. The RTC is unaffected by the change to the display clock. In this way, the RTC may differ from the display clock. The difference between the RTC and the display clock is hereinafter referred to as an offset.

The mobile phone 16 includes an elapsed time counter. The counter is initiated when the mobile phone 16 is initially configured. The counter continues to run regardless of changes to a display clock on the mobile phone 16. For example, the display clock of the mobile phone 16 may be automatically set by a cellular carrier while the mobile phone 16 is connected to a network operated by the cellular carrier or may be manually set by the patient. Further, the display clock of the mobile phone 16 may automatically change during events such as crossing time zones or a change to daylight savings time. For example, the display clock of the mobile phone 16 may be set relative to Greenwich Mean Time (GMT). When the mobile phone 16 is in a first time zone, the display clock of the mobile phone 16 may be set to GMT+5. Similarly, when the mobile phone 16 is in a second time zone, the display clock of the mobile phone 16 may automatically be changed to GMT+4, for example.

In one example, the diabetes management application 14 stores a snapshot time when the diabetes management application 14 is initiated. The snapshot time is a reference time based on a trusted time source. The diabetes management application 14 bases all time calculations (described below) on the snapshot time. In one example, the mobile phone 16 may be connected to a network, such as a cellular network or a WiFi network. When the mobile phone 16 is connected to the network, the snapshot time is set to a current GMT time. For example, the diabetes management application 14 communicates with a computing device remotely located from the mobile phone 16. The computing device may be part of the National Institute of Standards and Technology network. The diabetes management application 14 receives the current GMT time from the computing device.

When the mobile phone 16 is not connected to a network, the snapshot time is set to be equal to an RTC time of the meter 12. For example, the diabetes management application 14 requests a current RTC time from the meter 12. The diabetes management application 14 receives the current RTC time from the meter 12. The diabetes management application 14 stores the snapshot time in a memory associated with the mobile phone 16. The diabetes management application 14 uses the snapshot time as a reference time for calculating timestamps associated with received glucose measures. Further, the diabetes management application 14 tracks the amount of time elapsed since the snapshot time. This elapsed time may be referred to as an internal clock of the diabetes management application 14. For example, the internal clock of the diabetes management application 14 is equal to the amount of time that has elapsed on the counter of the mobile 16 since the snapshot time was taken. In other words, the internal clock is set to be equal to the snapshot time. The internal clock then keeps time by adding the elapsed time on the counter to the snapshot time.

Because of inherent inaccuracies of manually setting the display clock of the mobile phone 16, the display clock of the mobile phone 16 may differ from the internal clock of the diabetes management application 14. The diabetes management application 14 is configured to determine an accurate time that a glucose measure was taken based on the difference between the RTC of the meter 12 and the time on the internal clock of the diabetes management application 14. In some embodiments, the meter 12 communicates a current RTC time with the glucose measure. In another embodiment, the diabetes management application 14 requests a current RTC time from the meter 12. The diabetes management application 14 stores a time on the internal clock associated with the request for the current time on the RTC (i.e., the time at which the request was sent). The time associated with the request for the current time on the RTC is herein after referred to as a request time.

The diabetes management application 14 determines the difference between the request time and the current time on the RTC. The difference request time and the current time on the RTC is hereinafter referred to as a delta time. In an alternative implementation, the diabetes management application 14 determines whether the delta is greater than a predetermined threshold. The predetermined threshold may be a time equal to the amount of time that typically elapses between the diabetes management application 14 requesting the current RTC time and receiving a response from the meter 12. For example, the predetermined threshold may be 5 seconds. When the diabetes management application 14 determines the delta is greater than the predetermined threshold, the diabetes management application 14 stores the delta.

Conversely, when the diabetes management application 14 determines the delta is not greater than the predetermined threshold, the diabetes management application 14 disregards the delta. Alternatively, the diabetes management application 14 may set the delta equal to 0. Further, when the diabetes management application 14 determines the delta is greater than the predetermined threshold, the diabetes management application 14 may adjust the delta to account for the predetermined threshold. For example, the diabetes management application 14 may subtract 5 seconds from the delta time to account for the elapsed time between the diabetes management application 14 requesting the current RTC time and receiving a response from the meter 12.

The diabetes management application 14 stores the RTC of the meter 12, the offset, the counter time of the mobile phone 16, and the delta time. The diabetes management application 14 receives one or more glucose measures and a measurement time associated with each of the one or more glucose measures from the meter 12. The measurement time is equal to the time on the RTC when the glucose measurement was taken. The diabetes management application 14 may associate the one or more glucose measures with a timestamp. The timestamp may be referenced to as a reference time. The reference time is equal to the measurement time plus the delta time.

It is understood that while only one meter 12 is discussed, a patient may utilize multiple blood glucose (bG) meters in order to manage diabetes. Each of the multiple bG meters includes a distinct RTC. It is therefore understood that each of the multiple bG meters will also have a distinct RTC delta time. For example, another meter has another RTC. The RTC delta time for the other meter is the difference between the other RTC and the RTC of the meter 12.

In other words, the first meter (the meter 12 for example) to connect to the mobile phone 16 becomes the meter by which all delta times for all other devices subsequently connected are measured by. Further, measurements transmitted from the multiple meters will have associated timestamps. The associated timestamps are equal to a measurement time of the other RTC associated with a glucose measure transmitted by other meter plus the delta time of the meter 12 plus the distinct RTC delta time of the meter that transmitted the glucose measurement. The diabetes management application 14 stores all determined delta times associated with each of the meters in communication with the mobile phone 16.

In this way, when the counter on the mobile phone 16 is restarted, the diabetes management application 14 references the stored delta times for each of the meters. For example, the counter on the mobile phone 16 may be restarted when the mobile phone 16 is rebooted. The diabetes management application 14 is configured to reestablish time keeping between the mobile phone 16 and the meter 12. For example, when the counter on the mobile phone 16 is restarted, the diabetes management application 14 determines another snapshot time. The internal clock of the diabetes management application 14 is equal to the other snapshot time plus the elapsed time on the counter. The diabetes management application 14 receives a transmitted glucose measurement from the meter 12.

The diabetes management application 14 associates a timestamp with the glucose measurement. The timestamp is equal to a current RTC time plus the previously stored delta time associated with the meter 12. In other words, because the RTC time passes at the same rate as GMT time, the delta between the RTC time and the GMT time will remain constant and does not need to be reestablished. In some implementations, the delta time may be reestablished as a result of an RTC failure as described in detail below.

In some implementations, the diabetes management application 14 is configured to recover from an RTC failure. For example, an RTC failure is said to occur when a battery within the meter 12 is removed or no longer supplies power to the meter 12. The meter 12 may include a backup power supply. The backup power supply may be a capacitor that stores power supplied by the battery within the meter 12. The capacitor discharges the stored power when the battery is removed or no longer supplies power to the meter 12. The backup power supply may maintain the time on the RTC for a limited period of time, for example, 8 hours. If the meter 12 does not receive power from a battery or power source before the limited period of time expires, the RTC is reset. When the meter 12 is reinitiated (i.e., receives power from a batter or a power source) the meter 12 generates a failure signal. The meter 12 communicates the failure signal to the diabetes management application 14. The diabetes management application 14 reestablishes the delta time for the meter 12 in response to receiving the failure signal.

As described above, all other delta times associated with all other meters are based on the RTC of the meter 12. When the failure signal is received from the meter 12, the diabetes management application 14 reestablishes the delta time for the meter 12. Similarly, when the failure signal is received from a meter other than the meter 12, the diabetes management application 14 only reestablishes the delta time for the other meter. In other words, the diabetes management application 14 is configured to utilized previously stored delta times and only reestablishes delta times when an RTC failure occurs on the meter 12 or one of the other meters.

Figure 2:
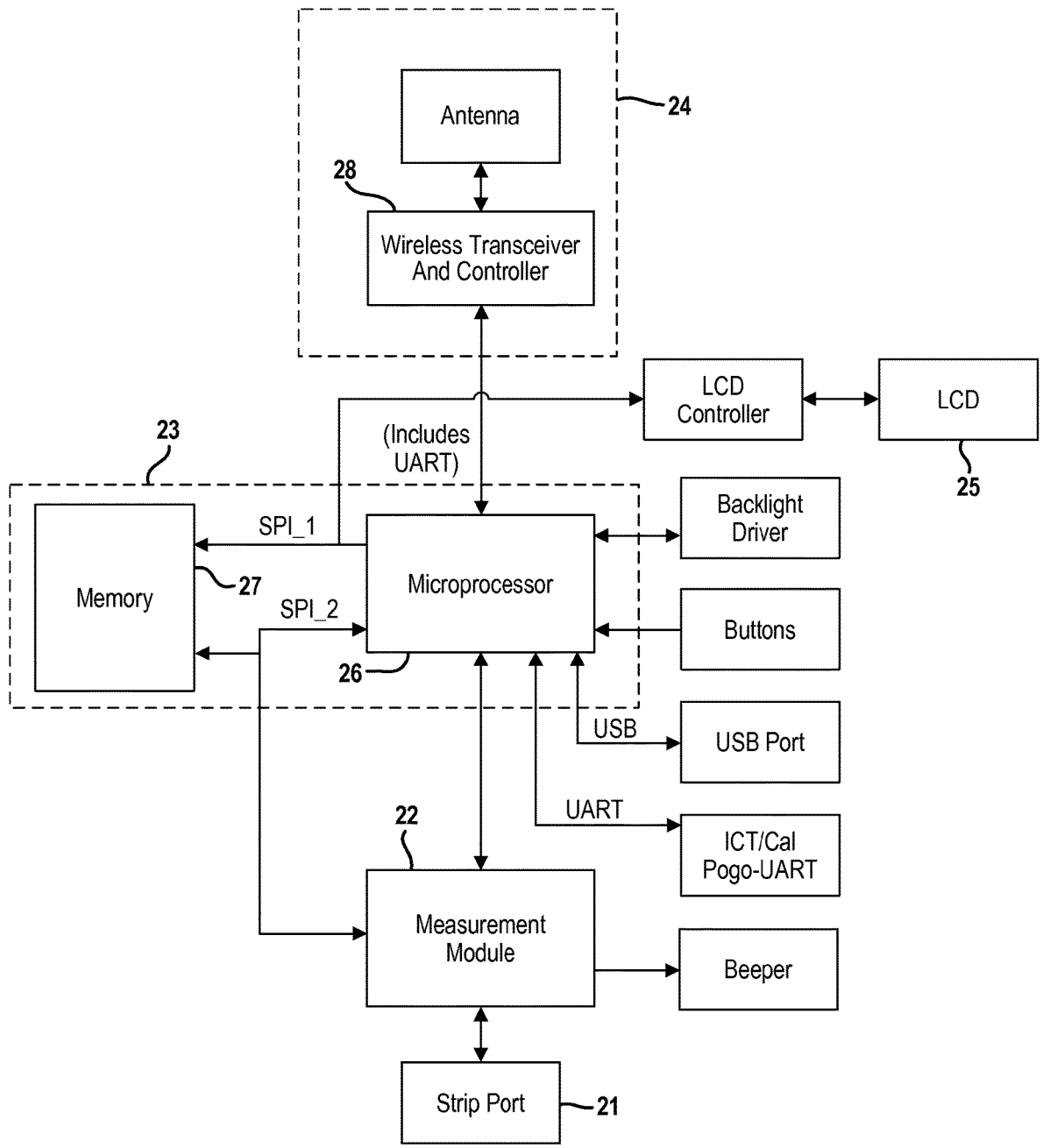
FIG. 2 is a block diagram of an exemplary hardware arrangement for the glucose meter.

FIG. 2 depicts an exemplary hardware arrangement for the glucose meter 12. The glucose meter 12 is comprised generally of a measurement module 22, a processing subsystem 23 and a communication subsystem 24. Each of these components is further described below. While the primary components are discussed herein, it is understood that other components (e.g., batteries) may be needed for the overall operation of the meter 12.

The measurement module 22 cooperatively interacts with a test strip inserted into a strip port 21 to determine a glucose measure from the sample of blood on the test strip. The measurement module 22 may include calibration information for the test strips being read by the meter 12. As used herein, the term module may refer to, be part of, or include an application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above. The term module may further include memory that stores code executed by the processor, where code, as used above, may include software, firmware, and/or microcode, and may refer to programs, routines, functions, classes, and/or objects.

The processing subsystem 23 is configured to receive the glucose measures from the measurement module 22 which may in turn be stored in memory by the processing subsystem 23. Glucose measures may also be displayed by the processing subsystem 23 on a display 25. The user can interact with the meter 12 using various user interface components, such as buttons, switches, a speaker, a microphone, USB port, etc. Each of these components is interfaced with the processing subsystem 23. In an exemplary embodiment, the processing subsystem 23 includes a microprocessor 26 and one or more volatile and/or non-volatile memories 27 although other implementations are envisioned for the processing subsystem.

The processing subsystem 23 is also interfaced with the communication subsystem 24. In an exemplary embodiment, the communication subsystem 24 includes a wireless transceiver 28. The wireless transceiver 28 operates to communicate the glucose measures and other data wirelessly via a data link to a remote device physically separated from the meter 12. The communication subsystem 24 can also include an antenna, microcontroller, voltage and power control circuits and a flash memory device. Although a few primary components of the meter 12 are discussed herein, it is readily understood that other components (e.g., power source) may be needed to implement the meter 12.

Figure 3:
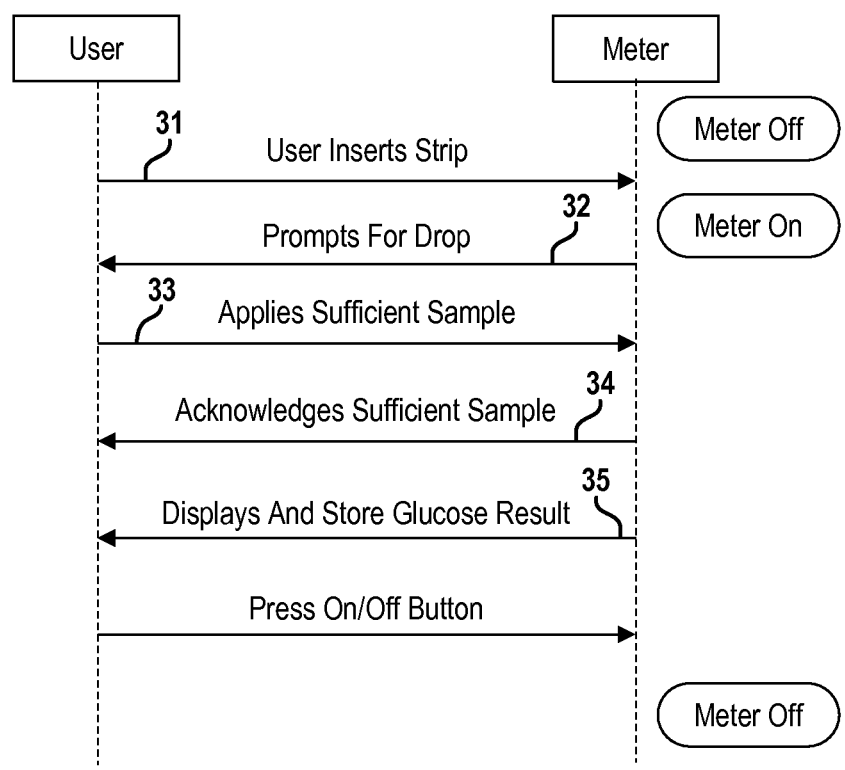
FIG. 3 is a sequence diagram illustrating an exemplary sequence for taking a blood glucose measure using the glucose meter.

FIG. 3 depicts an exemplary sequence for taking a blood glucose measure using the blood glucose meter 12. The user may insert a test strip at 31 into a port of the glucose meter 12. Insertion of the test strip prompts the glucose meter 12 to power on. The user may alternatively power on the glucose meter 12 using an on/off button. In this case, the glucose meter 12 will prompt the user to insert a test strip. The user may also power on the glucose meter 12 without having inserted a test strip into the meter. In any of these cases, the glucose meter 12 may perform a quality check on the test strip inserted into the meter 12. Once the quality check has been completed, the meter 12 is ready to perform a test.

To begin a test, the user is prompted at 32 for a sample of blood. In response to the prompt, the user provides a blood sample at 33 using the test strip, where the test strip includes a reaction site that receives the blood sample from the patient. Upon receipt of the blood sample, the glucose meter 12 will proceed to analyze the blood sample in a manner readily known in the art. Before doing so, the glucose meter 12 may acknowledge the sufficiency of the blood as indicated at 34.

During the analysis, a blood glucose measure is obtained from the blood sample. The blood glucose measure will be displayed to the user and stored on the glucose meter 12 as indicated at 35. Stored glucose measures may be uploaded subsequently from the glucose meter 12 in a batch manner to a physician's computer.

Figure 4:
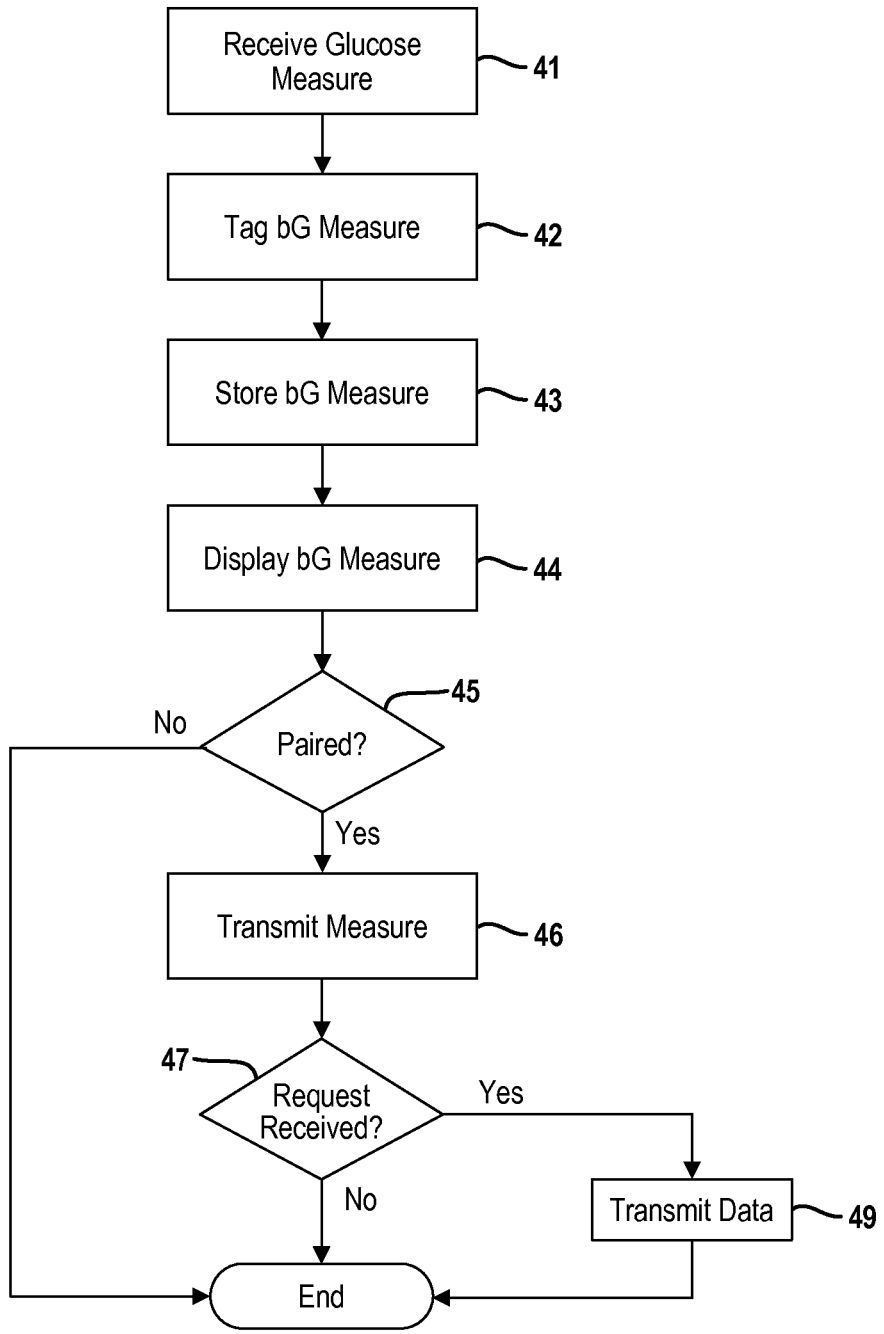
FIG. 4 is a flowchart illustrating an exemplary technique for transmitting blood glucose measures individually from the glucose meter.

Rather than sending blood glucose measures in a batch manner, the glucose meter 12 may be configured to transmit blood glucose measures individually as shown in FIG. 4. The blood glucose measures may be transmitted, for example to a mobile phone, such as the mobile phone 16, or some other portable computing device carried by the user. Because the mobile phone 16 is typically in close proximity to the user, it may be used as a data collector for the patient's blood glucose measures. A diabetes management application 14 residing on the mobile phone 16 can then be used for data analysis as well as other sophisticated diabetes management functions. Consequently, the processing power and memory available on the glucose meter 12 can be streamlined, thereby reducing the cost of the glucose meter 12.

Upon determining a blood glucose measure, the blood glucose measure is first tagged at 42 with identifying information. The glucose measure may be tagged by the meter or tagged by the user. Identifying information may include but is not limited to a timestamp for when the measure was taken, a serial number for the meter, the meter type, other information pertaining to the test strip, and patient added comments. For example, the patient may add comments that include flags indicating the measurement was taken before a meal, after a meal, before bedtime, or other subjective health information. Of note, each blood glucose measure is also tagged with a unique sequence number assigned by the glucose meter.

In one embodiment, a counter is incremented each time a glucose measure is taken and the value of the counter is assigned to the blood glucose measure. The sequence number may be used to retrieve missing data from the glucose meter 12 as is further described below. Once tagged, the blood glucose measure is stored at 43 in a memory of the glucose meter 12 and displayed to the user at 44 on a display of the glucose meter 12. It is understood that the glucose meter 12 may store and display the blood glucose measure prior to tagging the blood glucose measure with the additional information. Further, in some embodiments, the glucose meter 12 does not store or display the blood glucose measure.

Next, the glucose meter 12 determines at 45 whether it is paired via a wireless data link with another device, such as mobile phone 16. The current blood glucose measure is transmitted at 46 to the mobile phone when the glucose meter 12 is paired to the mobile phone. While reference is made throughout this disclosure to a message being sent with a single glucose measure, it is envisioned that in some embodiments the message transmitted by the glucose meter 12 can contain one or more glucose measures.

In one embodiment, the blood glucose measure is transmitted automatically and without user intervention. For example, after taking a glucose measure, the glucose measure is transmitted automatically after a predefined timeout period (e.g., five seconds) without receiving any input from the user. In another embodiment, the blood glucose measure is transmitted automatically in response to the user navigating away from the measurement result screen. In a similar manner, the blood glucose measure may be transmitted automatically in response to the meter 12 being powered down by the user. It is envisioned that the mobile phone and/or the diabetes management application 14 is authenticated with the glucose meter 12 during the pairing process.

The glucose meter 12 may also receive a request for missing glucose measures at 47 from the diabetes management application 14. In one embodiment, the request identifies any missing glucose measures by its sequence number as will be further described below. In response to receiving a request, the glucose meter 12 will transmit the missing glucose measures at 49 to the diabetes management application 14. It is to be understood that only the relevant steps are discussed in relation to FIG. 4 but that other software-implemented instructions may be needed to transmit data from the glucose meter 12. In an exemplary embodiment, the method described above is implemented by a user interface module residing on the glucose meter 12.

Figure 5:
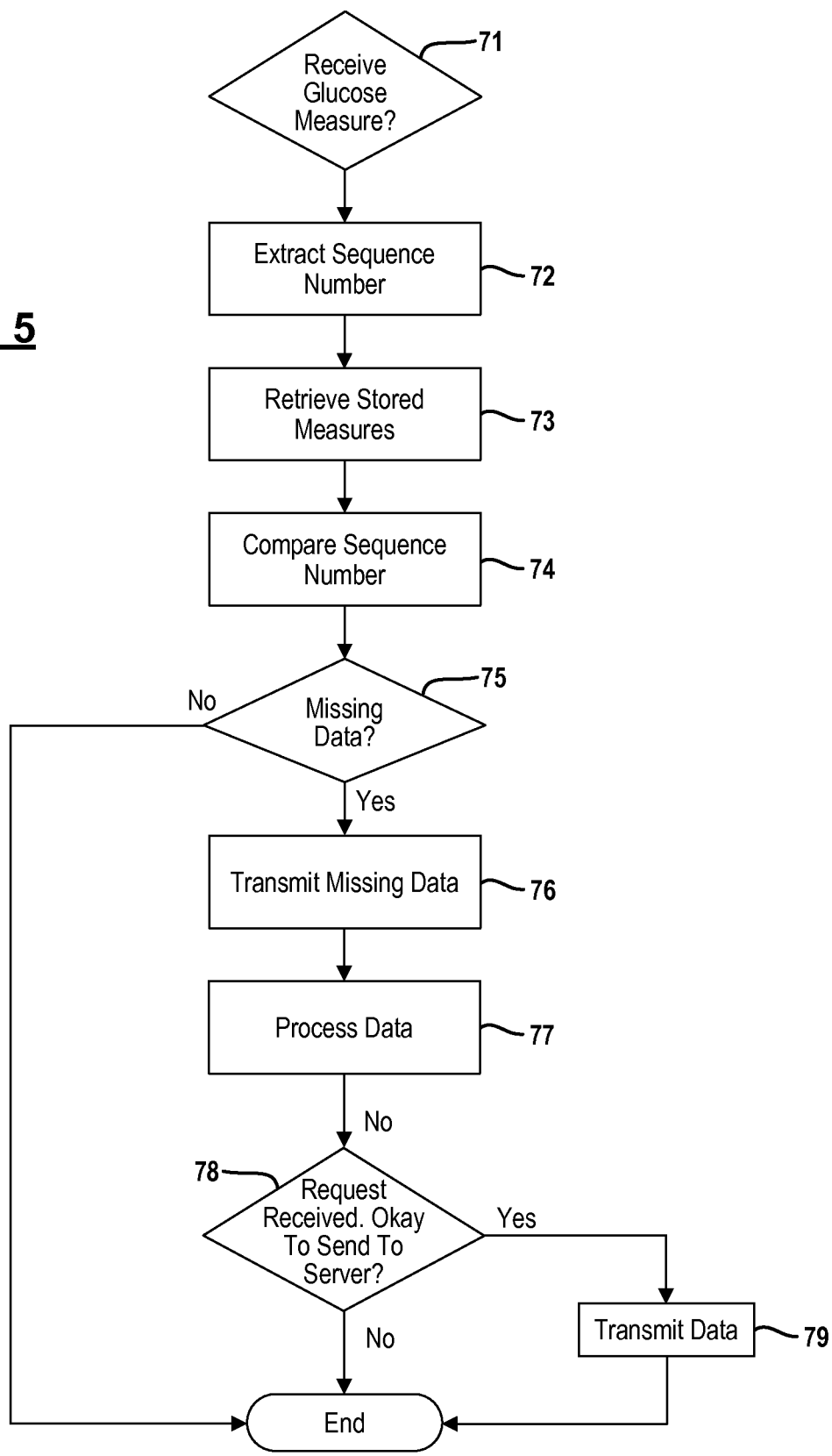
FIG. 5 is a flowchart illustrating an exemplary technique for processing glucose measures received by the diabetes management application.

FIG. 5 depicts an exemplary method for processing glucose measures received by the diabetes management application 14 residing on the mobile phone 16. In the exemplary embodiment, glucose measures are transmitted individually to the diabetes management application 14 as described in relation to FIG. 4. It is envisioned that other techniques for transmitting the glucose measure to the diabetes management application 14 are contemplated by this disclosure. For example, the glucose meter 12 may transmit the glucose measures via a WiFi connection, a Bluetooth connection, a cable connection, or any other suitable data transfer connections and/or protocols.

Upon receiving a glucose measure at 71, a sequence number associated with the glucose measure is first determined by the diabetes management application 14. A unique sequence number is assigned by the glucose meter 12 to each glucose measure as described above. Thus, the sequence number associated with the glucose measure can be extracted at 72 from the data packet or message received from the glucose meter 12. In some embodiments, a series of glucose measures previously received from the glucose meter 12, along with their associated sequence numbers, may be stored in a memory device and thus accessible to the diabetes management application 14. In other embodiments, only the most recently received glucose measure and its sequence number is stored by the diabetes management application 14. In either case, the stored glucose measure(s) along with associated sequence number(s) are retrieved from memory.

A comparison is made at 74 between the sequence number extracted from the present glucose measure and the sequence numbers of the stored glucose measures. A request for missing glucose measures is transmitted by the diabetes management application 14 to the glucose meter 12 when an omission in the sequence is detected. For example, a request for missing glucose measures is transmitted when the extracted sequence number is 74 and the highest stored sequence number is either 71 or 72. Conversely, a request is not transmitted when the extracted sequence number is 74 and the highest stored sequence number is 73. Because this comparison is made for each glucose measure received by the diabetes management application 14, a comparison of the extracted sequence number only needs to be made to the highest stored sequence number. In other embodiments, the diabetes management application 14 may analyze the series of glucose measure for omitted measures and send a request for each glucose measure missing from the series of glucose measures. The request for missing glucose measures can be transmitted in accordance with the protocol described in relation to FIG. 1.

At 78 the diabetes management application 14 processes the glucose measures. For example, the diabetes management application 14 may associate the most recently received glucose measure with previously received glucose measures. The diabetes management application 14 may then generate a graphical representation of the glucose measures. The diabetes management application 14 displays the graphical representation on a screen of the mobile phone 16. The diabetes management application 14 may receive a request to transmit the glucose measure(s) to a remote location, such as the remote server 18.

At 79 the diabetes management application 14 determines whether a request was received from the remote server 18 to transmit the glucose measure(s) to the remote server 18. For example, a medical professional may request a patient's blood glucose measurements from the diabetes management application 14 in order to treat the patient. When the diabetes management application 14 determines that a request was received, the diabetes management application 14 transmits the glucose measure(s) to the remote server 18. Transmitting the glucose measure(s) may include packaging the glucose measure(s) in a packet configured to be received and interpreted by the remote server 18. In another embodiment, the diabetes management application 14 automatically transmits the glucose measure(s) to the remote server 16 upon receiving the glucose measure(s) from the meter 12.

Figure 6:
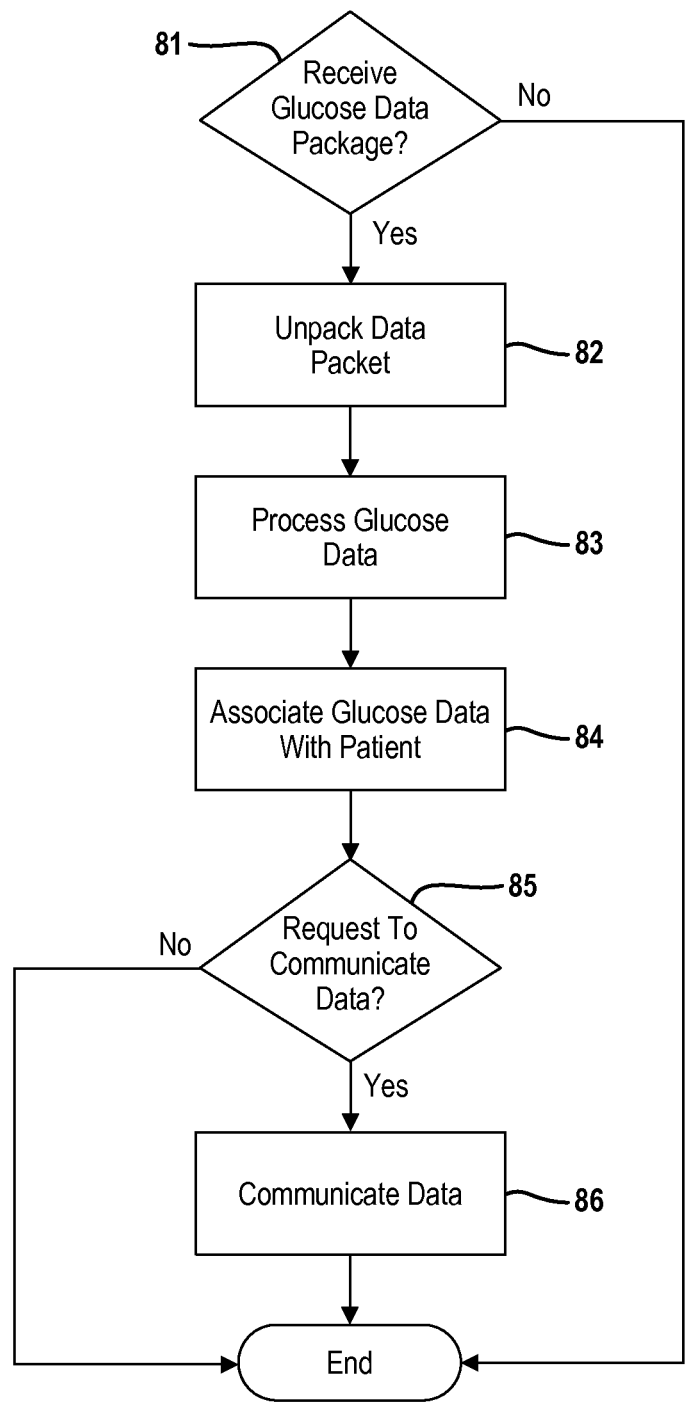
FIG. 6 is a flowchart illustrating an exemplary technique for processing glucose measures received by the remote server.

FIG. 6 depicts an exemplary method for processing glucose measures received by the remote server 18. The remote server 18 determines whether a glucose data packet was received from a remotely located computer device, such as the mobile phone 16 at 81. In another embodiment, the remote server 18 may receive a glucose data packet from a PC or other suitable computing devices. When the remote server 18 determines that a glucose data packet was received from the mobile phone 16, the remote server 18 unpacks the glucose data packet at 82. For example, the remote server 18 is configured to interpret the format of the glucose data packet. The glucose data may include, but is not limited to, one or more glucose measures, an associated patient name, and a timestamp correlating to the time the one or more glucose measures was collected.

At 83, the remote server 18 processes the glucose data. For example, the remote server 18 may associate the received glucose data with other relevant patient data previously received by the remote server 18. The remote server 18 may associate the one or more glucose measures with a plurality of previously received glucose measures pertaining to the same patient. In one embodiment, the remote server 18 may store the associated glucose measures relating to the patient in a patient database.

In some embodiments the remote server 18 is configured to allow a remote user to access the correlated glucose measures. For example, a physician of the patient may be granted access to review and make notes relating to the associated glucose measures, in order to treat the patient. Similarly, the patient may be granted access to review the patient's glucose trends.

At 85, the remote server 18 determines whether to communicate the glucose data to another computing device, such as the mobile phone 16 or the meter 12. For example, the remote server 18 may receive a request from the mobile phone 16 to communicate the glucose data. When the remote server 18 receives a request to communicate the glucose data, the remote server 18 packages and communicates the glucose measurements, associated timestamps, and other relevant and associated data to the mobile phone 16.

Figure 7:
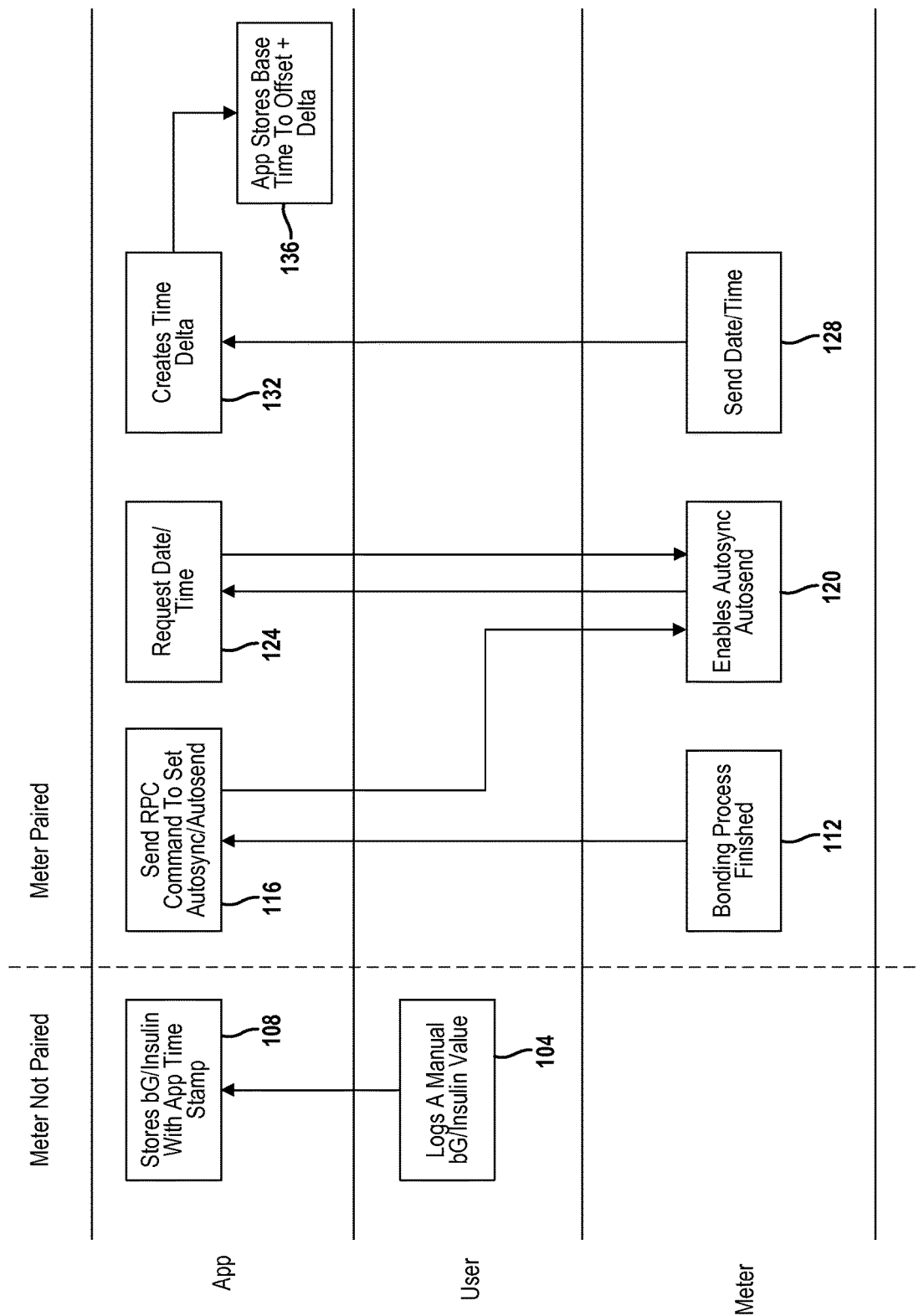
FIG. 7 is a flowchart illustrating an exemplary technique for time keeping between the glucose meter and the diabetes management application.

FIG. 7 depicts an exemplary method for time keeping between the glucose meter 12 and the diabetes management application 14. In an exemplary embodiment, the diabetes management application 14 determines whether the meter 12 is paired with the mobile phone 16. When the meter 12 and the mobile phone 16 are not paired, the patient (referred to as user in FIGS. 7 and 8) manually logs a blood glucose measure and/or an insulin value at 104. The patient may launch the diabetes management application 14 on the mobile phone 16 by selecting an icon representative of the diabetes management application 14.

The diabetes management application 14 first determines a snapshot time as described above. For example, when the mobile phone 16 is connected to a network, such as a cellular network or WiFi network, the diabetes management application 14 obtains the snapshot time from the network. When the mobile phone 16 is not connected to a network, the diabetes management application 14 stores a snapshot time equal to a current time of the RTC time of the meter 12. As described above, the diabetes management application 14 may request a current RTC time from the meter 12. Alternatively, the meter 12 may communicate a current RTC time with a glucose measure. The patient may then navigate to a data entry screen within the diabetes management application 14. The patient then enters data relevant to at least one of a blood glucose measure and an insulin value. The diabetes management application 14 stores the data, a timestamp, and a delta associated with the meter 12 at 108.

The timestamp is indicative of a time the at least one glucose measure was obtained and/or the insulin value was injected by the patient. In other words, when the patient manually enters a glucose measure, the patient also enters an accurate time that the measurement was taken. The diabetes management application 14 stores a timestamp equal to the time manually entered by the patient.

When the diabetes management application 14 determines the meter 12 is paired with the mobile phone 16, the diabetes management application 14 instructs the meter 12 to initiate an automatic synchronization application and an automatic send application at 116. The meter 12 enables the automatic send application and the automatic synchronization application at 120. While the automatic send application is active, the meter 12 automatically communicates received glucose measures and measurement times associated with each of the glucose measures to the mobile phone 16. The measurement times are equal to a time on the RTC at which a particular glucose measure was received by the meter 12. The automatic synchronization program is configured to determine a reference time for all glucose measures of the patient communicated to the mobile phone 16.

For example, as described above, the meter 12 includes an RTC and the mobile phone 16 includes an elapsed time counter. At 124, the diabetes management application 14 requests a current time and date from the RTC within the meter 12. At 128 the meter 12 communicates to the diabetes management application 14 an RTC time and date. At 132 the diabetes management application 14 determines a delta (as described above) based on the difference between the RTC time and a request time associated with the request for the current RTC time. The diabetes management application 14 stores the delta at 136. The diabetes management application 14 may also determine a delta for other glucose measuring devices the patient may operate.

The diabetes management application 14 associates a timestamp with each of the received glucose measures. The timestamp is equal to the measurement time associate with the glucose measure plus the delta. For example only, the RTC may have a current time of 13:00 hours and the internal clock time is 12:00 hours. In this example, the delta is minus 1 hour. The diabetes management application 14 receives a first glucose measurement from the meter 12 with a measurement time equal to 13:30 hours on the RTC clock of the meter 12. The diabetes management application 14 generates a timestamp of 13:30 hours minus 1 hour. The diabetes management application 14 stores the first glucose measurement with a timestamp of 12:30.

The diabetes management application 14 may receive another glucose measurement from another meter. The other meter includes another RTC. The other RTC has a current time of 11:00 hours at a time when the RTC of the meter 12 has a current time of 13:00 hours. The other meter has an RTC delta time of plus 2 hour. (i.e., the difference between the other RTC and the RTC of the meter 12 as described above). The diabetes management application 14 receives the other glucose measurement and a measurement time equal to 12:45 hours on the other RTC clock. The diabetes management application 14 generates a time stamp of 12:45 hours plus 1 hour (i.e., the other RTC delta time plus the other RTC delta time). The diabetes management application 14 stores the other glucose measurement with a timestamp of 13:45.

In this way, the diabetes management application 14 ensures an accurate reference time for each received glucose measure from the meter 12 and the other meter regardless of the relative device times. By utilizing the RTC of the meter 12 and an RTC delta of the other meter, the diabetes management application 14 can determine an actual period between patient glucose measures. For example, the diabetes management application 14 can determine how much time elapsed between each measurement regardless of an actual clock time of the meter 12, the other meter, and the counter of the mobile phone 16.

Figure 8:
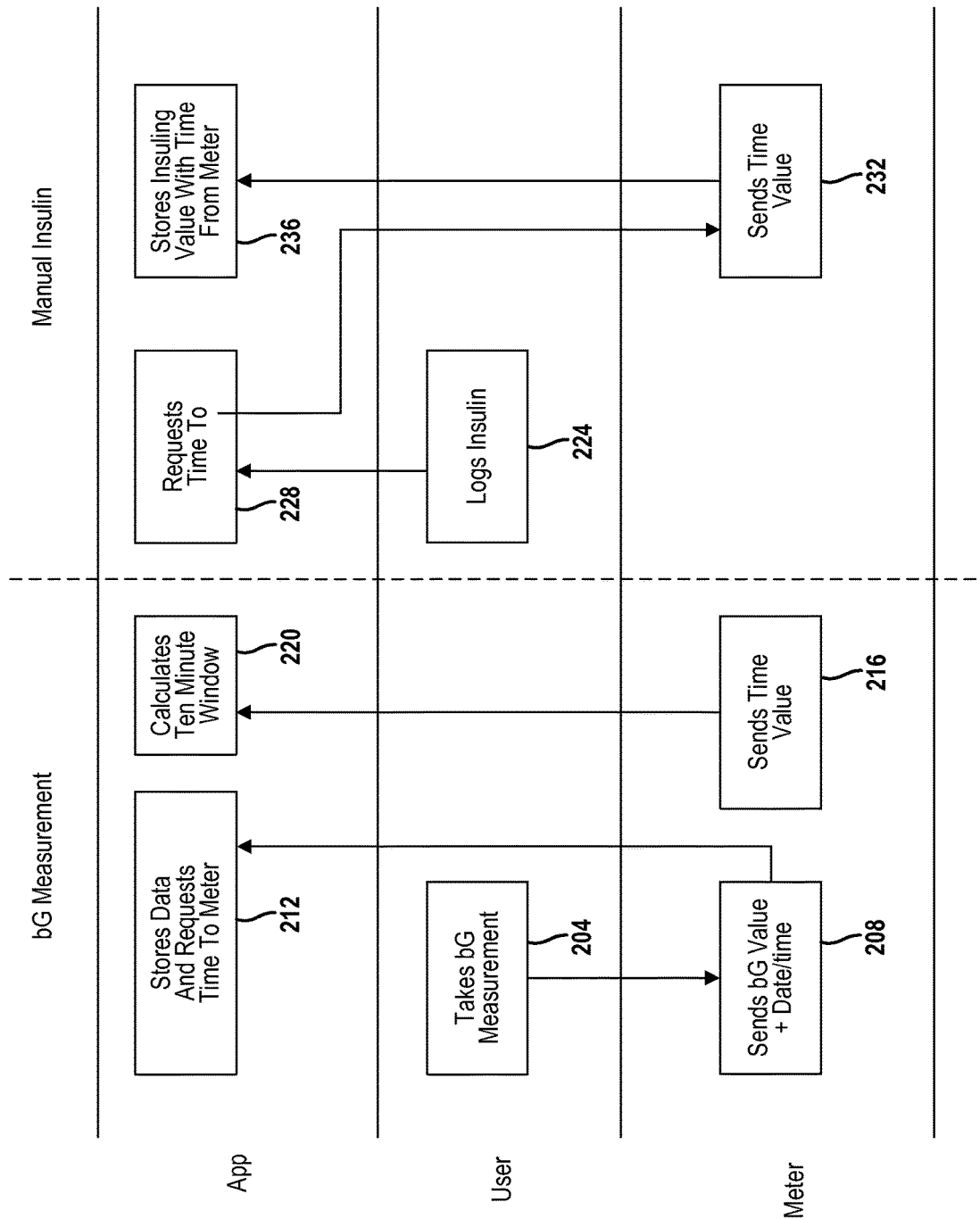
FIG. 8 is a flowchart illustrating an exemplary technique for recording glucose measures and insulin values in the diabetes management application.

FIG. 8 depicts an exemplary method for recording glucose measures and insulin values in the diabetes management application 14. In an exemplary embodiment, the diabetes management application 14 receives glucose measures and insulin values relating to the patient. At 204 the patient takes a blood glucose measurement utilizing the meter 12. The meter 12 automatically sends the blood glucose measurement and an associated timestamp to the diabetes management application 14.

The diabetes management application 14 stores the received blood glucose measurement and timestamp. It can be appreciated that the timestamp may differ from the time at which the data is communicated to the diabetes management application 14. For example only, the meter 12 and the mobile phone 16 may not be continuously paired or within range to be able to communicate. Consequently, the meter 12 may automatically send stored measurements when the meter 12 is within a range to communicate with the mobile phone 16. Because an undefined period may have elapsed since the measurements were taken and stored within the meter 12, the timestamp associated with a measurement may be relatively old compared to the time when the meter 12 communicates the measurements to the mobile phone 16. The diabetes management application 14 processes the received blood glucose measurement. For example, the diabetes management application 14 determines a bolus calculation based on the blood glucose measurement.

The diabetes management application 14 may also generate a bolus recommendation based on the bolus calculation. For example only, the bolus recommendation may include instructing the patient to take an amount of insulin or to consume carbohydrates in order to increase or decrease the patient's blood glucose. In order for the diabetes management application 14 to recommend an effective bolus recommendation, the bolus recommendation must occur within a predetermined period following the timestamp of the blood glucose measurement. For example, the predetermined period may be less than 10 minutes. The diabetes management application 14 determines whether the timestamp is within the predetermined period. The diabetes management application 14 generates a request to the meter 12 to communicate a current RTC time at 212. At 216, the meter 12 communicates a current RTC time to the diabetes management application 14.

At 220 the diabetes management application 14 determines whether the timestamp is within the predetermined period. For example, the diabetes management application 14 determines the difference between the timestamp and the current RTC time. When the difference is less than the predetermined period, the diabetes management application 14 generates a bolus recommendation. When the difference is greater than the predetermined period, the diabetes management application 14 does not generate a bolus recommendation. The diabetes management application 14 may instruct the patient to determine a current glucose measurement.

At 224, the patient manually logs an insulin value in the diabetes management application 14. The diabetes management application 14 generates a request for the meter 12 to communicate an RTC time at 228. The meter 12 communicates a current RTC time to the diabetes management application 14 at 232. At 236, the diabetes management application 14 associates the delta time of the meter 12 with the received insulin value and the time on the internal clock of the diabetes management application 14 when the glucose measurement was received. The diabetes management application 14 may generate a bolus recommendation based on the insulin value and at least one glucose measurement.

Figure 9:
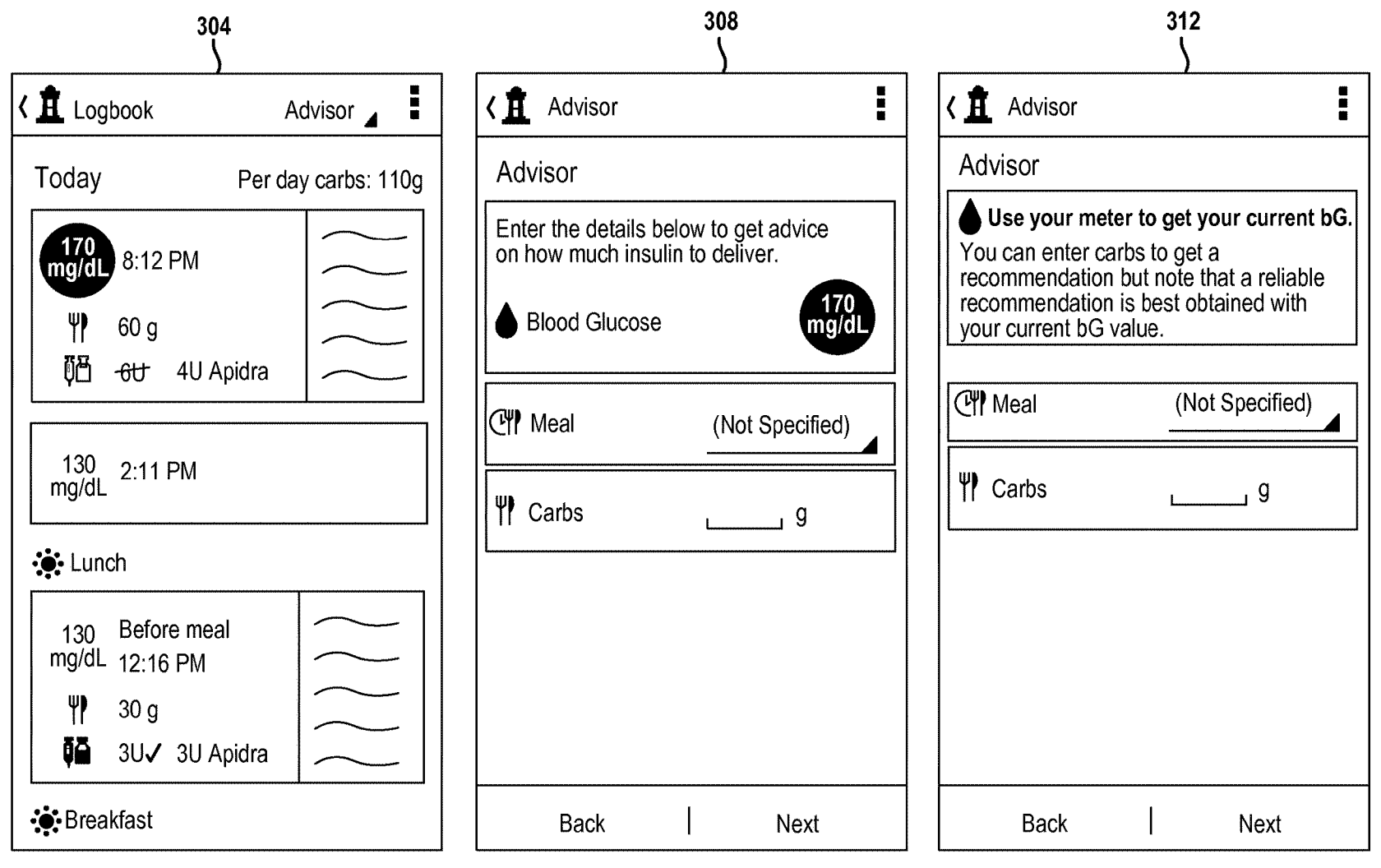

FIG. 9 depicts exemplary screenshots of the diabetes management application 14. In an exemplary embodiment, the diabetes management application 14 is configured to communicate glucose relevant data to the patient. For example, the diabetes management application 14 generates a plurality of reports based on data received from the patient. The diabetes management application 14 may display the plurality of reports on the display screen of the mobile phone 16. The plurality of reports may include, but is not limited to, a daily patient glucose summary, a patient glucose history report, a bolus recommendation, and a request for information input screen.

The diabetes management application 14 may generate the daily patient glucose summary based on the one or more glucose measures received from the meter 12. The glucose summary may also include data manually recorded by the patient, such as meal information and insulin values. An example daily patient glucose summary is shown at 304. The daily patient glucose summary may be formatted to display the patient's bolus calculation before and after a meal. Further, the daily patient glucose summary may display data relating to whether or not the patient followed a previously recommended insulin value. For example, the diabetes management application 14 may make an insulin value recommendation based on a bolus calculation. The patient may then inject the recommended insulin value and record the injection in the diabetes management application 14.

Conversely, the patient may decide to inject a different insulin value than the recommended value. The patient then records the different insulin value in the diabetes management application 14. The diabetes management application 14 compares the recommended insulin value to the recorded insulin value. When the recorded insulin value equals the recommended insulin value, the diabetes management application 14 displays an indication (such as a green check mark) on the daily patient glucose summary. When the recorded insulin value does not equal the recommended insulin value, the diabetes management application 14 displays an indication (such as a red slash or no symbol) on the daily patient glucose summary. In this way, the diabetes management application 14 communicates a graphical representation of the patient's adherence to the bolus recommendation.

The diabetes management application 14 may generate a request for information input screen as shown at 308 and 312. The request for information input screen may include a display of previously received data. For example, the request for information input screen may display a previously recorded glucose measurement. The request for information input screen advises the patient to input specified information. For example, the specified information may include meal information, and the total number of carbohydrates the patient has consumed or will consume. Additionally or alternatively, the specific information may include health events or physical activity indicators that influence the recommended bolus insulin. The diabetes management application 14 stores the specified information. The diabetes management application 14 may generate a bolus recommendation based on the specified information.

Figure 10:
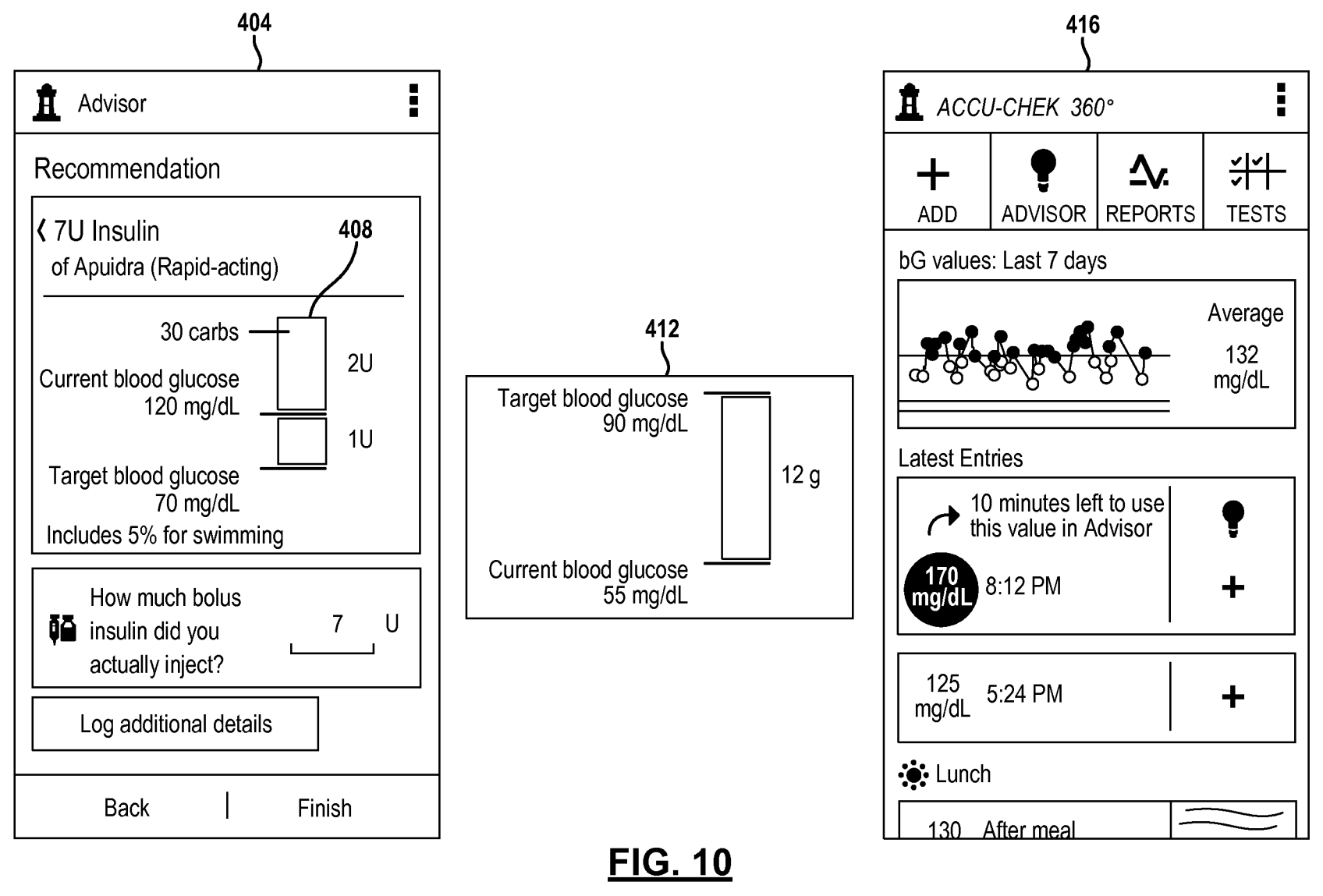
Figure 11:
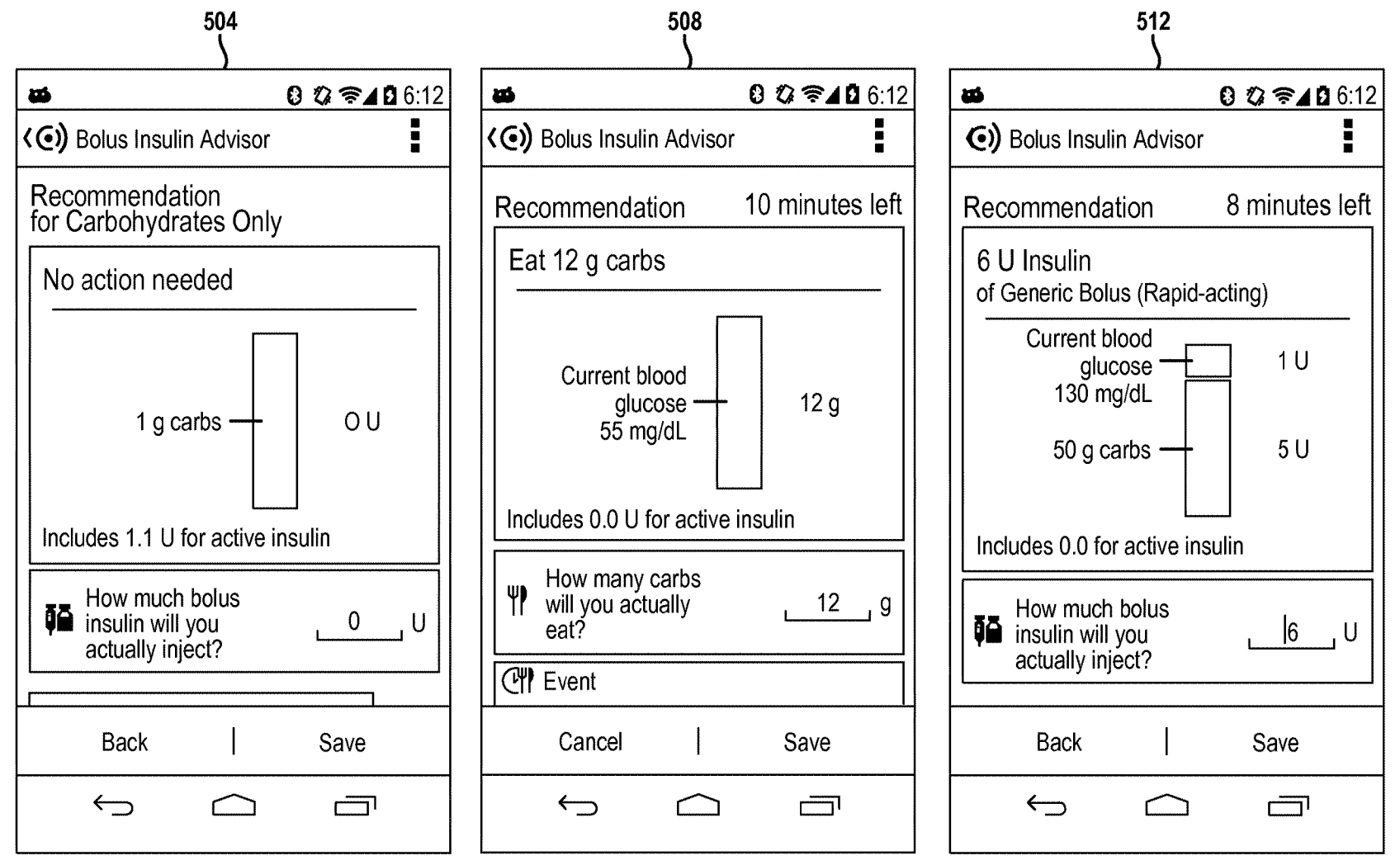

FIGS. 10 and 11 depict further exemplary screenshots of the diabetes management application 14. At 404, a bolus recommendation screenshot is shown. Alternative bolus recommendation screenshots are shown at 504, 508, and 512. The diabetes management application 14 determines whether to determine a bolus calculation based on the one or more glucose measures. For example, the diabetes management application 14 determines whether a timestamp associated with the one or more glucose measures occurred within a predetermined period. The predetermined period may be 10 minutes, for example. When the diabetes management application 14 determines the timestamp is within the predetermined period, the diabetes management application 14 determines a bolus calculation. Conversely, when the diabetes management application 14 determines the timestamp is not within the predetermined period, the diabetes management application 14 does not determine a bolus calculation. Further, the diabetes management application 14 may generate an indication to the patient. The indication may include communicating to the patient that the one or more glucose measures is not timely or current. The indication may further include instructing the patient to transmit another glucose measure.

The diabetes management application 14 determines a bolus calculation based on the one or more glucose measurements received from the meter 12 and manually recorded patient data, such as insulin values and meal information. The diabetes management application 14 generates the bolus recommendation based on the bolus calculation. In one embodiment, the diabetes management application 14 utilizes visual indicators to communicate bolus information to the patient. The diabetes management application 14 utilizes a color code in order to visually alert the patient of a current status of the patient's blood glucose.

For example, the diabetes management application 14 generates a blood glucose indicator 408 based on the bolus calculation. The diabetes management application 14 colors the blood glucose indicator 408 blue when the patient's glucose is greater than a predetermined upper threshold. The diabetes management application 14 colors the blood glucose indicator 408 red when the patient's glucose is less than a predetermined lower threshold as shown at 412. The diabetes management application 14 colors the blood glucose indicator 408 green when the patient's glucose is between the predetermined upper threshold and the predetermined lower threshold. Alternatively, the diabetes management application 14 does not display a color coded indication when the patient's glucose is between the predetermined upper threshold and the predetermined lower threshold as shown in FIG. 11 at 504. Additionally, the patient may enter an actual amount of insulin the patient will inject.

In this way, the diabetes management application 14 visually alerts the patient of the patient's current blood glucose. Accordingly, the patient can quickly ascertain whether or not the patient's glucose is within an acceptable range, above a range, or below a range. The patient may then follow the recommendation in the bolus recommendation in order to increase, decrease, or maintain the patient's glucose. For example, when the diabetes management application 14 color codes a bolus recommendation blue, the bolus recommendation may recommend an amount of insulin for the patient to inject. The diabetes management application 14 requests the patient to input an amount of insulin the patient actually injected. The diabetes management application 14 compares the recommended amount of insulin to the actual injected amount of insulin. The diabetes management application 14 may continue to repeat the process described above.

When the diabetes management application 14 color codes a recommendation red, the advisor recommends the patient consume an amount of carbohydrates. The diabetes management application 14 requests the patient input the actual amount of carbohydrates the patient consumed. The diabetes management application 14 compares the recommended amount of carbohydrates to the actual amount of carbohydrates. The diabetes management application 14 may continue to repeat the process described above.

When the diabetes management application 14 color codes a bolus recommendation green, the bolus recommendation may include instructing the patient to consume carbohydrates or inject insulin in order to maintain a current blood glucose. Additionally or alternatively, the diabetes management application 14 may allow the patient to input an actual injected amount of insulin. Further, the diabetes management application 14 may not color code a bolus recommendation. For example, the bolus recommendation may be displayed in a default text color of the mobile phone 16.

The diabetes management application 14 also communicates a patient glucose history report. An exemplary patient glucose history report is shown at 416. The diabetes management application 14 may generate the patient glucose history report based on a plurality of received patient glucose measurements, manually recorded patient data, previously calculated bolus recommendations, and previously documented actual bolus amounts.

The patient glucose history report may include a color code, such as the color code described above. For example, the diabetes management application 14 may chart patient glucose values over a period of time. The diabetes management application 14 may apply the same color code to each of a plurality of patient glucose values based on whether the value was greater than a predetermined upper threshold, less than a predetermined lower threshold, or between the predetermined upper threshold and the predetermined lower threshold when the value was recorded. The diabetes management application 14 may communicate the patient glucose history report to the patient by displaying the report on the display screen of the mobile phone 16. The patient may review the report in order to determine glucose trends of the patient.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

What is claimed is:

1. A system for time keeping between multiple devices used by a patient to manage diabetes, the system comprising:
a handheld medical device that includes:
a port configured to receive a test strip having a reaction site for receiving a sample of fluid from a patient;
a real-time clock (RTC); and
a blood glucose (bG) meter, cooperatively operable with a test strip inserted in the port, configured to measure glucose in a sample of fluid residing in the test strip and associate a first measurement time with the glucose measurement;
a mobile computing device comprising a processor configured to execute a diabetes management application stored on an associated memory and a counter that begins counting time in response to the mobile computing device being initiated;
the diabetes management application is operable to:
determine a snapshot time;
set an internal clock of the diabetes management application equal to the snapshot time and keep time on the internal clock by using the counter;
determine whether the handheld medical device is paired with the mobile computing device;
selectively instruct the handheld medical device to communicate the glucose measurement and the first measurement time in response to a determination that the handheld medical device is paired with the mobile computing device;
request a current device time from the RTC;
determine a first device delta time by determining a difference between the current device time and a time on the internal clock;
associate a first timestamp with the glucose measurement, wherein the first timestamp is equal to the first measurement time plus the first device delta time;
determine whether a difference between the first measurement time and another current time of the RTC is less than a predetermined value, wherein the diabetes management application requests the another current time from the RTC of the handheld medical device; and
generate, in response to the determination that the difference is less than the predetermined value, a recommendation for a quantity of insulin for the patient, where the recommendation is based in part on the glucose measurement.

2. The time keeping system of claim 1 wherein the diabetes management application is operable to determine whether the mobile computing device is connected to a network.

3. The time keeping system of claim 2 wherein the diabetes management application is operable to set, in response to the mobile computing device being connected to a network, the snapshot time equal to a current Greenwich Mean Time (GMT).

4. The time keeping system of claim 2 wherein the diabetes management application is operable to set, in response to the mobile computing device not being connected to a network, the snapshot time equal to a current RTC time.

5. The time keeping system of claim 1 further comprising at least one other medical device configured to associate a second measurement time with a second glucose measurement and to transmit the second glucose measurement and the second measurement time to the diabetes management application.

6. The time keeping system of claim 5 wherein the diabetes management application is operable to determine a second device delta time for the at least one other medical device.

7. The time keeping system of claim 6 wherein the second device delta time is equal to the difference between an RTC time on the at least one other medical device and the RTC of the handheld medical device.

8. The time keeping system of claim 7 wherein the diabetes management application is operable to associate, with the second glucose measurement, a second timestamp equal to the second measurement time plus the second device delta time and the first device delta time.

9. A computer-implemented method for determining a measurement time associated with a blood glucose measure received from a glucose meter, the method comprising:
maintaining a clock accessible to a diabetes management application residing on a computing device, wherein the computing device includes a processor configured to execute the diabetes management application stored on an associated memory and a counter that begins counting time to maintain the clock in response to the computing device being initiated;
receiving, by the diabetes management application, a current time from a real-time clock via a communication link from a glucose meter, where the real-time clock is maintained on the glucose meter and the glucose meter is located remotely from the computing device;

receiving, by the diabetes management application, a blood glucose measure via the communication link from the glucose meter, where the blood glucose measure has a measurement time associated therewith and the measurement time is taken from the real-time clock maintained on the glucose meter;

determining, by the diabetes management application, a difference between time of the clock maintained by the diabetes management application and the current time received from the real-time clock;

storing, by the diabetes management application, the blood glucose measure, along with an updated measurement time, in a data store residing on the computing device, where the updated measurement time is set equal to the measurement time plus the difference;

determining, by the application, whether a difference between the measurement time and another current time of the real-time clock is less than a predetermined value;

generating, by the application and in response to the determination that the difference between the measurement time and the other current time of the real-time clock is less than the predetermined value, a recommendation for a quantity of insulin for the patient, where the recommendation is based in part on the glucose measure;

requesting, by the application and in response to the determination that the difference between the measurement time and the other current time of the real-time clock is greater than the predetermined value, a second blood glucose measure; and generating, by the application and in response to receiving the second blood glucose measure, the bolus recommendation based in part on the second glucose measure.

10. The computer-implemented method of claim 9 further comprising determining, by the application, whether the computing device is connected to a network.

11. The computer-implemented method of claim 10 further comprising setting, by the application and in response to the computing device being connected to a network, the clock equal to a current Greenwich Mean Time (GMT).

12. The computer-implemented method of claim 10 further comprising setting, by the application and in response to the computing device not being connected to a network, the clock equal to a current RTC time.

13. The computer-implemented method of claim 9 further comprising receiving, by the application, another glucose measurement and another measurement time associated therewith from another glucose meter.

14. The computer-implemented method of claim 13 further comprising storing, by the application, an updated measurement time associated with the other glucose measurement, in the data store residing on the computing device.

15. The computer-implemented method of claim 14 wherein the updated measurement time associated with the other glucose measurement is set equal to the other measurement time plus the difference between the time of the clock maintained by the diabetes management application and plus a difference between a time of the real-time clock residing on the glucose meter and a time of a real-time clock residing on the other glucose meter.

16. The computer-implemented method of claim 9 wherein the bolus recommendation comprises a color coded blood glucose indicator indicative of a current blood glucose level.

17. The time keeping system of claim 1 wherein the diabetes management application is operable to:
- request, in response to the determination that the difference between the measurement time and the other current time from the RTC is greater than the predetermined value, a second glucose measurement from the handheld medical device; and
- generate, upon receipt of the second glucose measurement, the bolus recommendation based in part on the second glucose measurement.

* * * * *